| United States Patent [19] | [11] | 4,057,624 |
|---|---|---|
| Hase et al. | [45] | Nov. 8, 1977 |

[54] COSMETIC EMULSIONS CONTAINING ACRYLAMIDE COPOLYMER

[75] Inventors: Brigitte Hase, Erkrath; Joachim Galinke, Langenfeld; Bernd Wegemund, Haan, all of Germany

[73] Assignee: Henkel Kommanditgesellschaft auf Aktien, Dusseldorf, Germany

[21] Appl. No.: 670,382

[22] Filed: Mar. 25, 1976

[30] Foreign Application Priority Data

Mar. 29, 1975 Germany ............................ 2514098

[51] Int. Cl.² ............................................. A61K 31/74
[52] U.S. Cl. .............................. 424/78; 424/DIG. 2; 424/168
[58] Field of Search ................................ 424/78, 168

[56] References Cited

U.S. PATENT DOCUMENTS 3,927,199  12/1975  Micchelli et al. ...................... 424/78
3,950,510  4/1976  Adams ..................................... 424/78

FOREIGN PATENT DOCUMENTS 2,423,849  12/1974  Germany ............................... 424/78

*Primary Examiner*—Dale R. Ore
*Attorney, Agent, or Firm*—Hammond & Littell

[57] ABSTRACT

Water-in-oil emulsions wherein the emulsifier is a copolymer of 1 mol of acrylamide with 2 to 20 mols of at least one ethylenically unsaturated ester copolymerizable therewith selected from the group consisting of vinyl alkylcarboxylates, alkyl and cycloalkyl acrylates, and alkly and cycloalkyl methacrylates, wherein the alkyl and cycloalkyl groups contain 6 to 24 carbon atoms, and the continuous phase is a cosmetically acceptable oil, which can be prepared easily, safely and inexpensively. The emulsions are substantially odorless and are cosmetically acceptable for the care of the skin.

10 Claims, No Drawings

COSMETIC EMULSIONS CONTAINING ACRYLAMIDE COPOLYMER

FIELD OF THE INVENTION

The invention relates to cosmetic emulsions of the water-in-oil type having a content of copolymers of acrylamide and vinyl esters of alkylcarboxylic acids or alkyl (meth)acrylates as emulsifiers. The invention includes the emulsions themselves and methods for the preparation thereof.

RELATED ART

In contrast to the production of oil-in-water emulsions, only a limited number of emulsifying agents are available, the best of which are becoming increasingly scarce, for producing cosmetic emulsions of the water-in-oil type. Wool fat and its derivatives are still some of the most important emulsifying agents for producing creams of the water-in-oil type. However, despite their uncontested advantages, wool fat and its derivatives such as lanolin have certain disadvantages. Thus, conventional water-in-oil emulsifying agents based on wool fat and its derivatives impart a strong intrinsic odor to creams which contain them. This, in turn, requires strong performing which frequently cannot be tolerated by persons with sensitive skin. However, this influencing of the quality of the cream by a strong intrinsic odor is not only peculiar to wool fat and its derivatives, but also extends to lanolin-free water-in-oil emulsifying agents based on animal sterols, particularly those based on cholesterol. Furthermore, low molecular weight emulsifying agents, together with the effective substances of the cream, can be absorbed by the skin, which is not desirable in all cases.

The most widely known water-in-oil emulsifying agents for cosmetic purposes include, in addition to the said emulsifying agents based on wool, wax alcohols and sterols, and the oleic acid esters of various polyols, such as glycerine, pentaerythritol, trimethylolpropane and sorbitol. However, due to the unsaturated character of their acid component, the oleic acid esters have various disadvantages with respect to their technical use, so that there is a genuine need for new and suitable water-in-oil emulsifying agents.

OBJECTS OF THE INVENTION

One object of the present invention is the development of a cosmetic emulsion or cream of the water-in-oil type which can be prepared easily and safely from inexpensive materials without need for costly emulsifying equipment.

Another object of the invention is the development of a cosmetic emulsion of the above type which is substantially odorless and which, therefore, can find general acceptance when containing only a small and harmless amount of perfume.

A further object of the invention is the development of such an emulsion which is stable at an acid, neutral and alkaline pH.

An additional object of the invention is the production of a cosmetic emulsion of the above type wherein the emulsifier is a copolymer of one mol of acrylamide with 2 to 20 mols of at least one ethylenically unsaturated ester copolymerizable therewith selected from the group consisting of vinyl esters of alkylcarboxylic acids, alkyl and cycloalkyl esters of acrylic acid, and alkyl and cycloalkyl esters of methacrylic acid wherein the alkyl and cycloalkyl groups contain 6 to 24 carbon atoms, and 20% to 751 % by weight of water, and a cosmetically acceptable oily material as a continuous phase.

These and other objects of the present invention will become more apparent as the description thereof proceeds.

DESCRIPTION OF THE INVENTION

It has now been discovered that the drawbacks of the prior emulsifiers have been overcome and that the above objects are obtained by the discovery of cosmetic emulsions and creams of the water-in-oil type which consist essentially of (1) 2% to 20% by weight of a polymeric emulsifier capable of forming emulsions of the water-in-oil type, consisting essentially of a copolymer of one mol of acrylamide with 2 to 20 mols of at least one ethylenically unsaturated ester copolymerizable therewith selected from the group consisting of vinyl esters of alkylcarboxylic acids, alkyl and cycloalkyl esters of acrylic acid, and alkyl and cycloalkyl esters of methacrylic acid wherein the alkyl and cycloalkyl groups contain 6 to 24 carbon atoms, (2) 20% to 75% by weight of water, and (3) the remainder up to 100% by weight of a cosmetically acceptable oily material as the continuous phase, such as vegetable and animal fats, waxes, fatty alcohols, hydrocarbons, perfumes and further auxiliary substances normally present in cosmetic emulsions.

More particularly, the present invention relates to a cosmetic emulsion of the water-in-oil type consisting essentially of (1) from 2% to 20% by weight of a polymeric emulsifier capable of forming water-in-oil creams consisting of a copolymer of (a) acrylamide, and (b) esters selected from the group consisting of acrylates of the formula

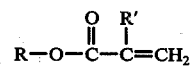

wherein R is a member having from 6 to 24 carbon atoms selected from the group consisting of alkyl, alkenyl, cycloalkyl and alkylcycloalkyl, and R' is a member selected from the group consisting of hydrogen and methyl, and vinyl alkylcarboxylates of the formula

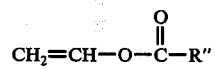

wherein R" is alkyl having from 5 to 24 carbon atoms, (2) from 20% to 75% by weight of water, and (3) the remainder to 100% by weight of a cosmetically acceptable oily material.

The emulsifying agents of the present invention can be produced by any of the generally known methods for the purpose. They can be produced in one processing step under the normal conditions of free radical polymerization. The polymerization can be carried out in non-polar solvents, such as benzene or toluene, or in polar solvents, such as methanol or tetrahydrofurane by means of peroxides, such as dibenzoyl peroxide or lauroyl peroxide, and azo compounds, such as azobisisobutyronitrile as free-radical polymerization catalysts.

The technical production is effected to best advantage in the form of solution polymerization in liquids which dissolve the monomers but which do not dissolve the polymers produced (precipitation polymerization), especially since polymers are produced which are satisfactorily precipitable and which are virtually free from monomers (J. Scheiber, Chemie und Technologie der Kunstlichen Harze, Vol. I, pp. 362 ff., 1961).

Monomeric starting compounds suitable for the preparation of the polymeric emulsifier, in addition to acrylamides are, for example:

vinyl caproate
vinyl caprylate
vinyl perlargonate
vinyl caprate
vinyl laurate
vinyl myristate
vinyl palmitate
vinyl isopalmitate
vinyl stearate
vinyl oleate
vinyl arachidate
vinyl behenate
hexyl acrylate
octyl acrylate
2-ethylhexyl acrylate
nonyl acrylate
decyl acrylate
lauryl acrylate
myristyl acrylate
cetyl acrylate
stearyl acrylate
oleyl acrylate
behenyl acrylate
tert. butylcyclohexyl acrylate
hexyl methacrylate
octyl methacrylate
nonyl methacrylate
decyl methacrylate
lauryl methacrylate
myristyl methacrylate
cetyl methacrylate
stearyl methacrylate
oleyl methacrylate
behenyl methacrylate.

Particular importance is attached to monomers wherein the alkyl component is the residue of a fatty alcohol having 8 to 14 carbon atoms, for example:

vinyl $C_{8-14}$ alkylcarboxylic, such as
vinyl caprate
vinyl pelargonate
vinyl caprinate, particularly vinyl laurate
vinyl myristate, as well as
$C_{8-14}$ alkyl (meth)acrylates, such as
octyl acrylate
nonyl acrylate
decyl acrylate
lauryl acrylate
myristyl acrylate
octyl methacrylate
nonyl methacrylate
decyl methacrylate
lauryl methacrylate
myristyl methacrylate.

In the emulsifiers of the present invention, the molar ratios of the acrylamide/ethylenically unsaturated comonomers are about 1:2 to 1:20, and preferably about 1:4 to 1:12.

The above-described copolymeric emulsifiers have average molecular weights between 2,000 and 100,000.

Those having average molecular weights between 3,000 and 20,000 are particularly suitable in view of the easy processability and the quality of the emulsions obtained. These molecular weights can be adjusted in a known manner by the amount of catalyst, the nature and amount of the solvent, and by adding polymerization or molecular weight regulators.

The emulsions in accordance with the invention are manufactured in a simple and known manner by dissolving the polymeric emulsifying agents in the oil phase at a temperature of approximately 60° C to 70° C. Subsequently, the desired quantity of water heated to approximately 60° C to 65° C is added, and the emulsion obtained is stirred while cooling. Cosmetically effective amounts of further constituents of the cosmetic emulsions to be manufactured, such as skin moisture regulators, vegetable extracts of effective substances, vitamines, hormones, pigments, salts, perfume, ultraviolet absorbers, dyestuffs, etc., are advantageously dissolved or distributed in the phase which absorbs these substances to best advantage. The required quantity of emulsifying agent is 2% to 20% by weight, preferably 5% to 10% by weight, relative to the total cosmetic emulsion. The amount of water to be incorporated can be 20% to 75% by weight, preferably 45% to 65% by weight, relative to the total cosmetic emulsion.

Products conventionally used, such as animal and vegetable oils and fats, synthetic esters of higher fatty acids with alkanols, higher fatty alcohols, waxes, so-called mineral fats and oils, such as paraffin oil, "Vaseline" ®, ceresine, silicone oils and silicone fats are suitable as the oily phase of the cosmetic emulsions in accordance with the invention. They should have melting points above 30° C and be substantially solid at room temperature. The oily phase represents the remainder of the weight of the total cosmetic emulsion.

German Offenlegungsschrift (DOS) No. 2,116,787 has already described the use of water-in-oil emulsifying agents in the form of sequence polymers which have at the same time at least one lipophilic sequence and one hydrophilic sequence. Each of the sequences should have the properties of the corresponding homopolymers. These sequence polymers are obtained by anionic polymerization which places high demands on the purity of the substances used, and requires working at low temperatures under protective gas and increased safety precautions when handling spontaneously inflammable catalysts. In contrast to this, the emulsifying agents required for producing the emulsions in accordance with the present invention can be manufactured in a simple manner.

In accordance with the German Offenlegungsschrift (DOS) No. 1,745,216, copolymers comprising a monomer having a lipophilic chain and a monomer having a carboxylic acid anhydride function are proposed as emulsifying agents for water-in-oil emulsions. However, such products are sensitive to hydrolysis and, to avoid this disadvantage, a further processing step in addition to polymerization is necessary in order to convert them into a more stable form.

In general, the emulsions in accordance with the present invention can also be used by persons having a sensitive skin. Since they do not have any appreciable intrinsic odor, they do not require heavy perfuming which, in turn, has an advantageous effect upon the compatibility and also saves costs.

Furthermore, the emulsions in accordance with the invention are distinguished by a low sensitivity to acid, thus rendering it possible to incorporate acidic raw materials therein, such as organic acids. A further very advantageous property of the emulsions in accordance with the invention is their high resistance to temperature, which enables them to withstand a thermal stress of 50° C for a period of 6 weeks without any detrimental effects.

The following examples are intended to further explain the invention, but without limiting the invention to these examples.

EXAMPLES

The following illustrates the preparation of two polymeric emulsifiers for use in cosmetic emulsions of the present invention.

EXAMPLE 1

Acrylamide/lauryl acrylate copolymer (1:3 molar ratio)

179.75 gm (0.75 mol) of lauryl acrylate were dissolved in 1610 gm of methanol. To this were added 2 gm of azoisobutyronitrile as catalyst. The solution was heated then to 60° C and maintained at that temperature for 6 hours with agitation. During the first two hours of heating, 17.75 gm (0.25 mol) of acrylamide dissolved in 160 gm of methanol were slowly added drop by drop. The copolymer precipitated during the course of the reaction. After the reaction was complete, the solvent was decanted off and the polymer was washed a few times with methanol. The product was 177 gm (90% of theory) of acrylamide/lauryl acrylate copolymer (1:3 molar ratio).

EXAMPLE 2

Acrylamide/vinyl laurate copolymer (1:3 molar ratio)

169.5 gm (0.75 mol) of vinyl laurate were dissolved in 400 gm of methanol. To the solution were added 2 gm of azoisobutyronitrile as catalyst. The resulting solution was heated to 60° C and maintained at this temperature for six hours with agitation. During the first two hours of heating, 17.75 gm (0.25 mol) of acrylamide dissolved in 160 gm of methanol were slowly added drop by drop. The copolymer precipitated during the course of the reaction. After the reaction was complete, the solvent was decanted off and the product was washed a few times with methanol. The product was 159 gm (85% of theory) of acrylamide/vinyl laurate copolymer (1:3 molar ratio).

The other copolymers, used in the examples given below, were obtained in an analogous manner to Examples 1 and 2.

EXAMPLE 3

Cosmetic emulsion based on Vaseline ®

A mixture of 10 gm of a 1:3 molar ratio acrylamide/vinyl laurate copolymer and 40 gm of Vaseline ® was melted together by heating to 65° C. To this were added with stirring 50 gm of water at 65° C. An emulsion readily formed, which was allowed to cool with continued stirring. The emulsion can be readily produced by manual stirring. The resulting cream was odorless and cosmetically acceptable. It was stable for several months and did not exhibit any change even after six weeks of storage at 50° C. This cream was a basic cosmetic which can be used to produce various cosmetic skin creams by addition of conventional cosmetic agents and perfume oils.

The following copolymers can be used in the foregoing example with the same satisfactory results in place of the acrylamide/vinyl laurate copolymer (1:3 molar ratio):

| Copolymer | Molar ratio |
| --- | --- |
| Acrylamide/vinyl laurate | (1:4) |
| Acrylamide/vinyl laurate | (1:10) |
| Acrylamide/vinyl caprylate | (1:15) |
| Acrylamide/vinyl caproate | (1:20) |
| Acrylamide/vinyl caprate | (1:8) |
| Acrylamide/vinyl caprate | (1:10) |
| Acrylamide/vinyl myristate | (1:4) |
| Acrylamide/vinyl isopalmitate | (1:3) |
| Acrylamide/vinyl myristate | (1:6) |
| Acrylamide/vinyl stearate | (1:2) |
| Acrylamide/lauryl acrylate | (1:3) |
| Acrylamide/lauryl acrylate | (1:6) |
| Acrylamide/nonyl methacrylate | (1:15) |
| Acrylamide/2-ethylhexyl acrylate | (1:10) |
| Acrylamide/decyl methacrylate | (1:8) |
| Acrylamide/decyl acrylate | (1:12) |
| Acrylamide/myristyl methacrylate | (1:4) |
| Acrylamide/lauryl methacrylate | (1:6) |
| Acrylamide/cetyl acrylate | (1:5) |
| Acrylamide/stearyl methacrylate | (1:2) |
| Acrylamide/2-ethylhexyl methacrylate | (1:10) |

EXAMPLE 4

Cosmetic emulsion based on hardened peanut oil/decyl oleate mixture

A mixture of 4 gm of acrylamide/vinyl laurate copolymer (1:3 molar ratio), 40 gm of a hardened peanut oil/decyl oleate mixture (90:10 by weight), 3 gm of beeswax, and 3 gm of glyceryl monooleate was melted together by heating to 70° C. To the melt were added 50 gm of water at 65° C with continuous agitation. An emulsion formed which was allowed to cool with continued agitation. A cream was obtained. Its stability properties were largely similar to those of the cream of Example 3.

Additional skin creams based on this basic cream can be produced by incorporating cosmetically effective amounts of conventional cosmetically effective substances such as skin moisture regulators, vegetable extracts, and perfume oils.

The following copolymers can be used with the same satisfactory results instead of the acrylamide/vinyl laurate copolymer (1:3 molar ratio) used above:

| Copolymer | Molar ratio |
| --- | --- |
| Acrylamide/vinyl myristate | (1:3) |
| Acrylamide/vinyl laurate | (1:3) |
| Acrylamide/vinyl myristate | (1:8) |
| Acrylamide/vinyl palmitate | (1:4) |
| Acrylamide/vinyl behenate | (1:2) |
| Acrylamide/decyl acrylate | (1:6) |
| Acrylamide/myristyl methacrylate | (1:3) |
| Acrylamide/lauryl methacrylate | (1:5) |
| Acrylamide/lauryl acrylate | (1:8) |
| Acrylamide/octyl acrylate | (1:12) |
| Acrylamide/behenyl acrylate | (1:2) |
| Acrylamide/lauryl myristyl acrylate | (1:6) |
| Acrylamide/tert. butylcyclohexyl acrylate | (1:8) |

EXAMPLE 5

Cosmetic emulsions based on Vaseline ®/decyl oleate mixture

A mixture of 7 gm of acrylamide/vinyl laurate copolymer (1:3 molar ratio), 10 gm of Vaseline ®, 15 gm of decyl oleate, 3 gm of beeswax, and 2 gm of calcium stearate was melted together by heating to 65° C. To the melt were added 63 gm of water at 65° C with stirring and agitation was continued until an emulsion was obtained. A cream was obtained, the stability properties of which were largely similar to those of the two creams described above.

A large number of cosmetic creams based on this basic cream can be produced by incorporating conventional cosmetically effective substances and perfume oils.

The acrylamide/vinyl laurate copolymer (1:3 molar ratio) acting as an emulsifying agent can be replaced with the same satisfactory results by the same weight of acrylamide/lauryl acrylate copolymer (1:3 molar ratio), acrylamide/ethylhexyl acrylate copolymer (1:10) and the other copolymers which have been mentioned.

EXAMPLE 6

Cosmetic emulsion based on hardened peanut oil

A mixture of 6 gm of acrylamide/ethylhexyl acrylate copolymer (1:10 molar ratio) and 44 gm of hardened peanut oil was melted together by heating to 65° C and to this were added, with stirring, 50 gm of water at 65° C. An emulsion was formed which was allowed to cool with continued stirring. The resulting cream had stability properties largely similar to those of the previously mentioned creams. The cream can act as a basic cream for various cosmetic preparations as described above.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A cosmetic emulsion of the water-in-oil type consisting essentially of (1) from 2% to 20% by weight of a polymeric emulsifier capable of forming water-in-oil creams consisting of a copolymer of (a) acrylamide and (b) esters selected from the group consisting of acrylates of the formula:

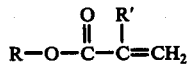

wherein R is a member having from 6 to 24 carbon atoms selected from the group consisting of alkyl, alkenyl, cycloalkyl and alkylcycloalkyl, and R' is a member selected from the group consisting of hydrogen and methyl, and vinyl alkylcarboxylates of the formula:

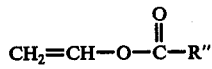

wherein R" is alkyl having from 5 to 24 carbon atoms, (2) from 20% to 75% by weight of water, and (3) the remainder to 100% by weight of a cosmetically acceptable oily material.

2. The cosmetic emulsion of claim 1 wherein said cosmetically acceptable oily material has a melting point above 30° C and is selected from the group consisting of vegetable fat, animal fat, wax, higher fatty alcohol, mineral and silicone oil.

3. The cosmetic emulsion of claim 1 wherein said polymeric emulsifier is present in an amount of from 5% to 10% by weight and said water is present in an amount of from 45% to 65% by weight.

4. The cosmetic emulsion of claim 1 wherein R is alkyl having from 8 to 14 carbon atoms.

5. The cosmetic emulsion of claim 1 wherein R" is alkyl having from 7 to 14 carbon atoms.

6. The cosmetic emulsion of claim 1 wherein the molar ratio of (a):(b) is 1:4 to 1:12.

7. The cosmetic emulsion of claim 1 wherein said polymeric emulsifier has an average molecular weight of from 2,000 to 100,000.

8. The cosmetic emulsion of claim 1 wherein said average molecular weight is from 3,000 to 20,000.

9. In the method of producing a cosmetic emulsion of the water-in-oil type comprising mixing an emulsifier capable of forming water-in-oil creams with a cosmetically acceptable oily material in the liquid phase at elevated temperatures, mixing therewith from 20% to 75% by weight of water, cooling under agitation and recovering said cosmetic emulsion of the water-in-oil type, the improvement consisting of adding from 2% to 20% by weight of a copolymer of (a) acrylamide and (b) esters selected from the group consisting of acrylates of the formula:

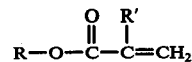

wherein R is a member having from 6 1 to 24 carbon atoms selected from the group consisting of alkyl, alkenyl, cycloalkyl and alkylcycloalkyl, and R' is a member selected from the group consisting of hydrogen and methyl, and vinyl alkylcarboxylates of the formula:

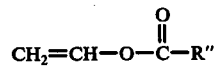

wherein R" is alkyl having from 5 to 24 carbon atoms, (2) from 20% to 75% by weight of water, and (3) the remainder to 100% by weight of a cosmetically acceptable oily material.

10. A composition which when emulsified with water forms a cosmetic emulsion of the water-in-oil type, consisting essentially of (1) from 2% to 20% by weight of a polymeric emulsifier capable of forming water-in-oil creams consisting of a copolymer of (a) acrylamide and (b) esters selected from the group consisting of acrylates of the formula:

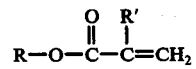

wherein R is a member having from 6 to 24 carbon atoms selected from the group consisting of alkyl, alkenyl, cycloalkyl and alkylcycloalkyl, and R' is a member selected from the group consisting of hydrogen and methyl, and vinyl alkylcarboxylates of the formula:

wherein R" is alkyl having from 5 to 24 carbon atoms, and (2) the remainder to 100% by weight of a cosmetically acceptable oily material, said emulsifier being dissolved in said oily material.

* * * * *

UNITED STATES PATENT OFFICE
CERTIFICATE OF CORRECTION

Patent No. 4,057,624          Dated Nov. 8, 1977

Inventor(s) BRIGITTE HASE, JOACHIM GALINKE and BERND WEGEMUND

It is certified that error appears in the above-identified patent and that said Letters Patent are hereby corrected as shown below:

| Col. | Line | |
|---|---|---|
| 2 | 2 | "751%" should be --75%-- |
| 4 | 3 | "Those" should not be the start of a new paragraph |
| 8 | 29 | "61 to 24" should be --6 to 24-- |

Signed and Sealed this

Twenty-fifth Day of April 1978

[SEAL]

Attest:

RUTH C. MASON
Attesting Officer

LUTRELLE F. PARKER
Acting Commissioner of Patents and Trademarks